(12) United States Patent
Aarestad et al.

(10) Patent No.: US 10,258,496 B2
(45) Date of Patent: *Apr. 16, 2019

(54) DEVICE AND METHOD FOR OPENING AN AIRWAY

(75) Inventors: Jerome Aarestad, Escondido, CA (US); Richard Rose, Rancho Santa Fe, CA (US); John Nelson, Redlands, CA (US); Donna Palmer, San Diego, CA (US)

(73) Assignee: SOMMETRICS, INC., Vista, CA (US)

( * ) Notice: Subject to any disclaimer, the term of this patent is extended or adjusted under 35 U.S.C. 154(b) by 19 days.

This patent is subject to a terminal disclaimer.

(21) Appl. No.: 12/838,669

(22) Filed: Jul. 19, 2010

(65) Prior Publication Data

US 2010/0275910 A1 Nov. 4, 2010

Related U.S. Application Data

(63) Continuation of application No. 12/002,515, filed on Dec. 17, 2007, now Pat. No. 7,762,263.

(60) Provisional application No. 60/874,969, filed on Dec. 15, 2006.

(51) Int. Cl.
*A61F 5/56* (2006.01)

(52) U.S. Cl.
CPC ........................................ *A61F 5/56* (2013.01)

(58) Field of Classification Search
USPC ................................................. 128/848, 846
See application file for complete search history.

(56) References Cited

U.S. PATENT DOCUMENTS

| | | | |
|---|---|---|---|
| 5,265,624 A | 11/1993 | Bowman | |
| 5,343,878 A | 9/1994 | Scarberry et al. | |
| 5,918,598 A | 7/1999 | Belfer et al. | |
| 5,979,456 A | 11/1999 | Magovern | |
| 6,877,513 B2 | 4/2005 | Scarberry et al. | |
| 6,935,335 B1 | 8/2005 | Lehrman et al. | |
| 7,182,082 B2 * | 2/2007 | Hoffrichter | 128/202.28 |
| 7,762,263 B2 | 7/2010 | Aarestead et al. | |
| 2003/0167018 A1 | 9/2003 | Wyckoff | |
| 2004/0025885 A1 | 2/2004 | Payne, Jr. | |
| 2005/0274386 A1 | 12/2005 | Macken | |
| 2005/0274387 A1 * | 12/2005 | MacKen | 128/848 |

(Continued)

FOREIGN PATENT DOCUMENTS

| | | |
|---|---|---|
| EP | 0330740 B1 | 9/1989 |
| WO | 1996034586 A1 | 11/1996 |
| WO | 2003075739 A2 | 9/2003 |

OTHER PUBLICATIONS

International Search Report and Written Opinion issued in PCT/US2007/025766 dated Jun. 12, 2008.

(Continued)

*Primary Examiner* — Victoria J Hicks
(74) *Attorney, Agent, or Firm* — Acuity Law Group, P.C.; Michael A. Whittaker

(57) ABSTRACT

A device and a method for creating and/or maintaining an obstruction free upper airway. The device is configured to fit under the chin of a subject adjacent to the subject's neck at an external location corresponding approximately with the subject's internal soft tissue associated with the neck's anterior triangle. The device is capable of exerting negative pressure on the surface of a subject's neck, displacing the soft tissue forward and enlarging the airway.

18 Claims, 11 Drawing Sheets

(56) References Cited

U.S. PATENT DOCUMENTS

2006/0266369 A1* 11/2006 Atkinson et al. ............ 128/848
2007/0221231 A1    9/2007 Macken

OTHER PUBLICATIONS

Prosecution history from U.S. Appl. No. 12/002,515, filed Dec. 17, 2007 now U.S. Pat. No. 7,762,263 issued Jul. 27, 2010.
Prosecution history from U.S. Appl. No. 90/009,989, filed Mar. 6, 2012 (documents dated Mar. 6, 2012 through Apr. 5, 2012)
Prosecution History from United States Reexamination Application No. 90/009,989, filed Mar. 6, 2012 (History from Mar. 6, 2012 to Sep. 25, 2012; 440 pages).

* cited by examiner

DEVICE AND METHOD FOR OPENING AN AIRWAY

CROSS-REFERENCE TO RELATED APPLICATIONS

This application is a continuation of U.S. application Ser. No. 12/002,515, filed, Dec. 17, 2007, entitled "DEVICE AND METHOD FOR OPENING AN AIRWAY," which in turn claims priority to U.S. Provisional Application No. 60/874,969, filed Dec. 15, 2006, both of which applications are hereby incorporated by reference in their entirety.

FIELD OF THE INVENTION

The present invention relates generally to medical devices. More particularly, the present invention relates to a device for creating and maintaining an obstruction free upper airway.

BACKGROUND OF THE INVENTION

Obstruction of the upper airway (that portion of the breathing passage which is outside of the thoracic cage) can occur at any age. Those at risk for having upper airway obstruction include person with sleep apnea, those with airway tumors or foreign bodies such as aspirated food, and those with inflammatory or traumatic damage to t the upper airway, which results in a weakened and collapsible airway wall, a condition known as tracheomalacia.

The medical sequalae of upper airway obstruction can be devastating: inability to effectively ventilate the lungs rapidly produces hypoxemia, a generalized condition of lowered blood oxygen. If left uncorrected, hypoxemia leads to serious and organ injury such as stroke and myocardial infarction (heart attack), and may have a lethal outcome.

Snoring is a common chronic medical problem that is associated with episodic partial upper airway obstruction during sleep. Snoring afflicts millions of people worldwide. Snoring can lead to chronic fatigue that follows sleep deprivation and is considered by many to be a serious medical problem. The sound of snoring is produced by turbulent air-flow moving through an area of partial upper airway obstruction that produces resonant vibrations in the soft tissues adjacent to the upper airway.

A percentage of those who snore also suffer from sleep apnea, another frequent and serious medical condition associated with episodic upper airway obstruction. In the most common type of sleep apnea, obstructive sleep apnea (OSA), an afflicted individual sustains numerous episodes of apnea, or complete, and often prolonged cessation of breathing. Severe cases may have 100 or more apnea events per hour of sleep. OSA results in nocturnal hypoxemia, and leads to cognitive impairment, daytime somnolence, hypertension, increased risk of stroke and myocardial infarction, and insulin resistant diabetes mellitus. Untreated, OSA may result in premature death.

OSA is caused by closure of the upper airway during sleep due to either alteration in the mechanical properties of the upper airway, and/or to disturbances in neuromuscular control over airway caliber. Alterations in the mechanical properties of the upper airway, which predispose to collapse of the upper airway during sleep, may be caused by anatomical conditions such as large tonsils, or may be idiopathic. A variety of medical interventions have been shown to improve the mechanical properties of the upper airway and reduce sleep related airway closure. These include upper airway remodeling surgeries, medical devices that re-position the mandible, and continuous positive airway pressure (CPAP).

Unfortunately, all current treatments produce results that are far from optimal. Surgery and re-positioning devices are effective in only a minority of OSA patients, and the responders cannot be identified with certainty prior to initiating treatment. As a result, many people are subjected to painful and expensive procedures without benefit. On the other hand, CPAP is effective in the majority of OSA patients; however, the treatment is uncomfortable and not well tolerated during long-term use. A substantial number of patients given CPAP discontinue therapy within the first year after initiation.

CPAP works by delivering air at pressures above ambient pressure to the upper airway during sleep. Application of positive pressure to the upper airway acts as a "stint" and can retard the tendency of the upper airway to collapse during certain stages of sleep in OSA patients. In order to deliver higher than ambient pressures to the upper airway, the patient must wear a tight fitting mask covering the mouth and/or nose. This mask is connected to an air supply tube, and a variable pressure air pump. An additional component can be added which humidifies the air, to avoid desiccation of the upper airway during treatment. There are multiple sources of patient dissatisfaction with CPAP including an uncomfortable face mask which may provoke feelings of claustrophobia, the noise of the air pump and the moisture of the humidification system. Also, some CPAP units are not easily portable and limit patients' ability to travel.

Therefore, there is a pressing medical need to develop a means of ameliorating obstruction of the upper airway, which is both highly effective and well tolerated during chronic use.

SUMMARY OF THE INVENTION

The foregoing needs are met by the present invention, wherein, in one aspect, a device is provided for applying pressure to an upper airway of a patient.

In accordance with one embodiment of the present invention, a device having a vessel is provided. The vessel can be a hollow or concave utensil, shaped as a cup, bowl, or the like. The vessel has an edge and an internal surface and is configured to fit under the chin of a subject adjacent to the subject's neck at an external location corresponding approximately with the subject's internal soft tissue associated with the neck's anterior triangle. The edge may include an adhesive surface. Additionally, a vacuum pump inlet is provided for receiving a negative pressure into the chamber to apply a force to a surface of the neck of the patient to draw the surface into the chamber. The device also includes a tube for connecting the vessel to the pressure control device. In addition, a pressure control device is provided for controlling the applied force within the range of about 0.5 kilogram to about 6.68 kilograms. In some embodiments, the applied force is within the range of about 0.61 kg to 6.14 kg. In other embodiments, the applied force is within the range of about 0.74 kg to 5.65 kg. In some embodiments, the applied force is within the range of about 0.91 kg to 5.2 kg. In some embodiments, the applied force is within the range of about 1.11 kg to 4.78 kg.

In certain embodiments, the vessel is made of a material having resilient memory such as silicone, urethane or rubber.

In certain embodiments, the pressure control device exerts the negative pressure within the interior chamber in the range of about 7.62 cm to about 60.96 cm of water. In certain embodiments, a vessel is dimensionally adapted to define an interior chamber for covering the anterior triangle of from about 32.90 cm² to about 210.58 cm² in surface area.

In certain embodiments, the device further includes a dynamic pump. The dynamic pump may be a regenerative pump or a centrifugal pump. In certain embodiments, the device includes a positive displacement pump. The positive displacement pump may be a vane pump, a diaphragm pump, or a linear pump.

Another embodiment of the present invention provides a method of applying a force to open an upper airway of a patient. According to the method, a vessel is placed against a surface of a patient's neck to seat an edge under the chin of the patient to form chamber at a location corresponding approximately with the patient's internal soft tissue associated with the neck's anterior triangle. A force in the range of from about 0.5 kilogram to about 6.68 kilograms is applied to the interior of the chamber to pull the neck's anterior triangle toward the interior chamber. The vessel may be located over the anterior triangle of the patient's neck to treat sleep obstructive sleep apnea and other disorders associated with upper airway obstruction.

Another embodiment of the present invention provides a method of treating obstructive sleep apnea.

In accordance with yet another embodiment of the present invention, a method of reducing snoring is provided. According to the method, a vessel having an opening is placed on the surface of a subject's neck. The vessel is configured to fit under the chin of a subject adjacent to the subject's neck at an external location corresponding approximately with the subject's internal soft tissue associated with the neck's anterior triangle. The vessel is attached at the opening to a tube having a first end and a second end. The first end of the tube is attached at the opening. Additionally, a vacuum source is attached to the second end of the tube. The vacuum source has a microprocessor and at least one acoustic sensor connected thereto. A force is applied over the anterior triangle of the patient's neck within the range of about 0.5 kilogram to about 6.68 kilograms. A signal corresponding with an acoustic signature of the subject is identified by the acoustic sensor. The signal is registered and processed with a microprocessor attached to the vacuum source. The level of negative pressure created at the vacuum source is automatically maintained to reduce and/or eliminate snoring. In certain embodiments, the acoustic sensor is a microphone There has thus been outlined certain embodiments of the invention in order that the detailed description thereof herein may be better understood, and in order that the present contribution to the art may be better appreciated. There are additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the present invention. The examples used herein are intended merely to facilitate an understanding of ways in which the invention may be practiced and to further enable those of skill in the art to practice the invention. Accordingly, the examples should not be construed as limiting the scope of the invention. In the drawings, like reference numerals designate corresponding parts throughout the several views.

DETAILED DESCRIPTION

Figure 1A:
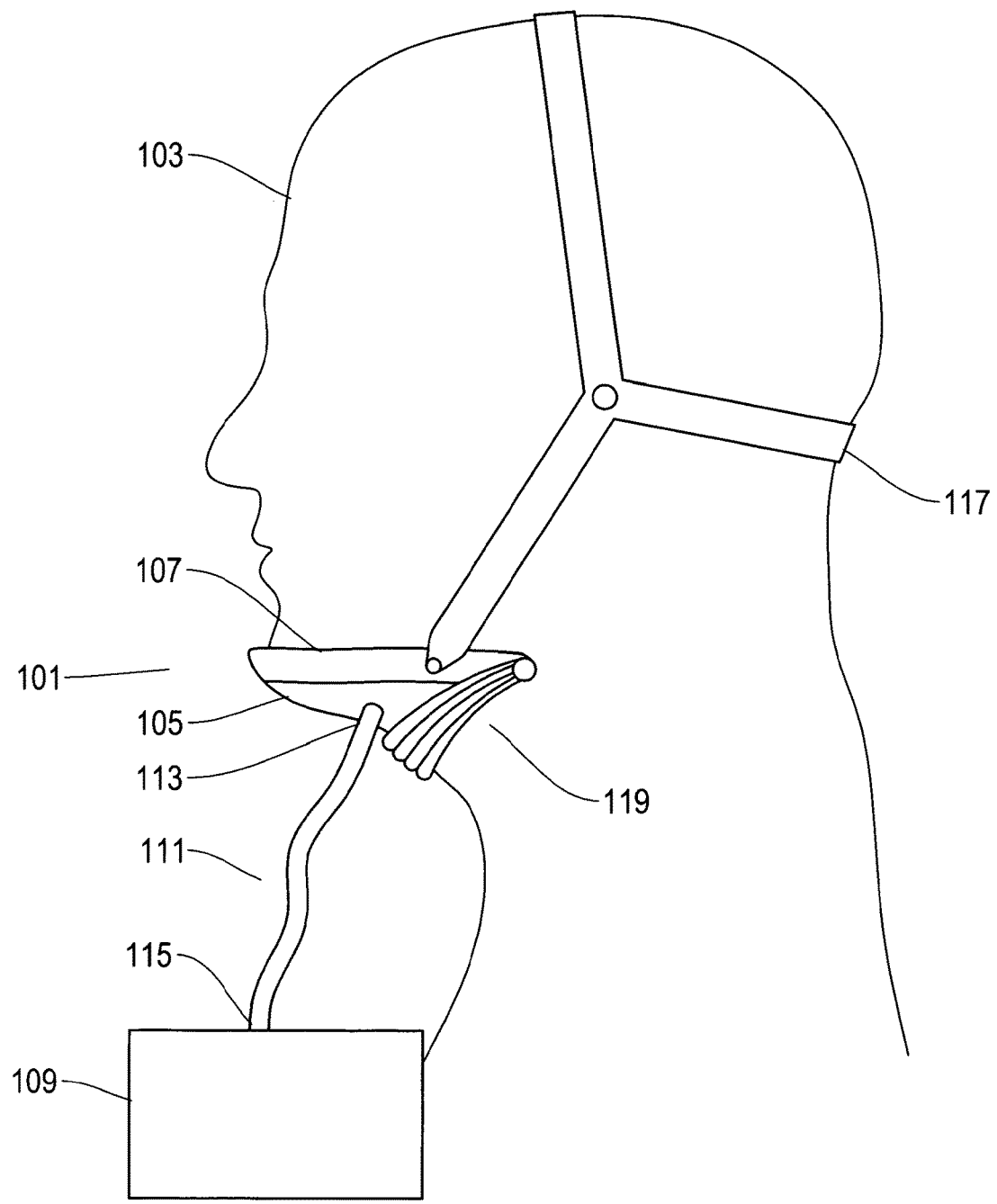
FIG. 1A is a view of the device according to an embodiment of the present invention on a subject.

The invention will now be described with reference to the drawing figures, in which like reference numerals refer to like parts throughout.

With reference to FIG. 1A, a device 101 is shown on a subject 103 according to an embodiment of the present invention. The device 101 includes a vessel 105, a vacuum source 109, a tube 111, and a pressure control (not shown). The vessel 105, among other things, includes an edge 107 and an internal surface (not shown). The edge 107 seats against the chin and neck of the patient to define a chamber at an external location approximately at the subject's internal soft tissue associated with the neck's anterior triangle.

According to the embodiment shown in FIG. 1A, a device 101 having a vessel 105 is worn by a subject. The vessel 105 is attached to a tube 111 at a first end 113 of the tube 111.

A second end 115 of the tube 111 is attached to a vacuum source 109. The vessel 105 is attached to the subject 103 by a strap 117.

The vessel 105 may be a hollow or concave utensil. In a non-limiting example, the vessel 105 may be shaped as a cup, bowl, or the like. The vessel may be formed, molded, or fabricated from any material. Non-limiting examples of such materials suitable for constructing the vessel 105 include plastics, metals, natural fabrics, synthetic fabrics, and the like. The vessel 105 may also be constructed from a material having resilient memory such as silicone, rubber, or urethane.

Additionally, the vessel 105 can be flexible, semi-rigid, or rigid. For purposes of the present invention, "semi-rigid" means partially or somewhat rigid. "Flexible" means capable of being bent, usually without breaking, or susceptible of modification or adaptation. "Rigid" means stiff or unyielding, not pliant nor flexible.

As shown in FIG. 1A, the strap 117 functions to attach and helps seal the vessel 105 on the surface of the skin of the subject 103. In alternative embodiments, the vessel 105 may be attached to a surface of a subject's neck by a negative pressure exerted by the vacuum source 109. Alternatively, adhesive may be utilized to attach the vessel 105 to a surface of the subject's neck. Additionally, the natural anatomical contours of a subject may act in a synergistic manner with any other known means or method of attachment, thereby increasing the effectiveness of the attachment. Further, the natural anatomical contours of the subject may, on its own, act to attach the vessel 105 to the surface of a subject's neck. All would serve as a sufficient means for attaching the vessel 105 on a surface of the subject's neck.

In alternative embodiments, a seal could be created by, for example, an adhesive, the natural anatomical contours of the subject, or at least one clamp, such as a differential clamp and the like. In one embodiment, the edge 107 has a high contact pressure area with the skin of the subject's neck. Upon exertion of negative pressure by the vacuum source 109, a seal is created. In alternative embodiments, the seal is created by the application of adhesive to the device 101 or the skin of a subject's neck in a desired area. In some embodiments, the seal may be an elastomeric seal. The elastomeric seal may comprise external flaps, extensions or the like, attached to the vessel 105. In one embodiment the elastomeric seal may be attached to the edge 107. The elastomeric seal may be made from materials including, but not limited to: Natural Rubber (NR); Polyisoprene (IR); Butyl rubber (copolymer of isobutylene and isoprene, IIR); Halogenated butyl rubbers (Chloro Butyl Rubber: CIIR; Bromo Butyl Rubber: BIIR); Polybutadiene (BR); Styrene-butadiene Rubber (copolymer of polystyrene and polybutadiene, SBR); Nitrile Rubber (copolymer of polybutadiene and acrylonitrile, NBR), also called buna N rubbers; Hydrated Nitrile Rubbers (HNBR) Therban® and Zetpol®; Chloroprene Rubber (CR), polychloroprene, Neoprene, Baypren; EPM (ethylene propylene rubber, a copolymer faeces of polyethylene and polypropylene) and EPDM rubber (ethylene propylene diene rubber, a terpolymer of polyethylene, polypropylene and a diene-component); Epichlorohydrin rubber (ECO); Polyacrylic rubber (ACM, ABR); Silicone rubber (SI, Q, VMQ); Fluorosilicone Rubber (FVMQ); Fluoroelastomers (FKM, FPM), for example, Viton®, Tecnoflon®, Fluorel® and Dai-El®; Perfluoroelastomers (FFKM); Tetrafluoro ethylene/propylene rubbers (FEPM); Chlorosulfonated Polyethylene (CSM), (Hypalon®); Ethylene-vinyl acetate (EVA); Thermoplastic Elastomers (TPE), for example, Hytrel®, Santoprene®; Polyurethane rubber; Resilin, Elastin; and Polysulfide Rubber.

FIG. 1A illustrates bellows 119 attached to the vessel 105. In the embodiment shown, the bellows 119 allow the subject 103 to maintain natural head motion while still allowing the vessel 105 to be effectively sealed against the skin of the subject 103. In one embodiment, the bellows 119 are formed from the same material as the vessel 105. In alternative embodiments, the bellows 119 may be formed from other suitable materials.

In one embodiment, the bellows 119 have no stiffness in a lateral sense to allow for increased movement of the subject. However, the lateral stiffness of the bellows can vary depending on the lateral movement desired. With regard to circumferential stiffness, the bellows 119 are rigid enough so that the vessel 105 does not collapse. In some embodiments, the vessel does not have a bellow.

Figure 1B:
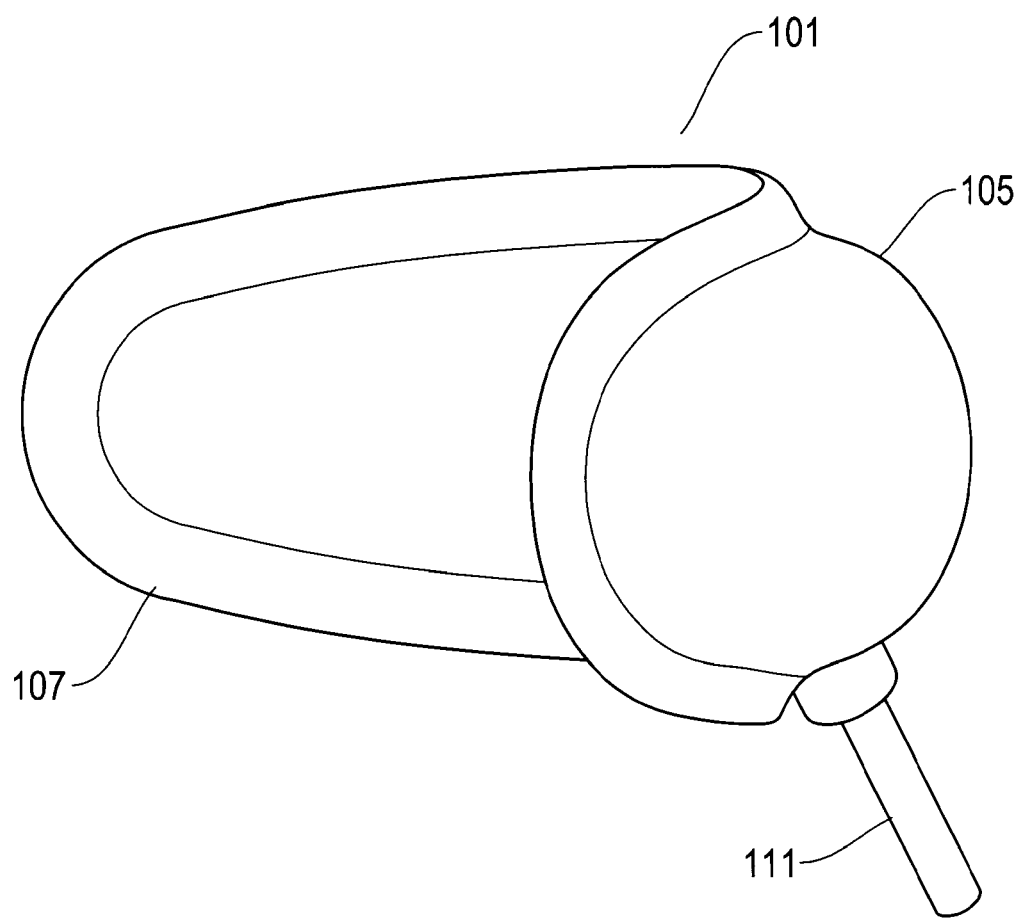
FIG. 1B shows a perspective view of the device according to an embodiment of the present invention.

FIG. 1B shows an alternative embodiment of the device 101. The device 101 includes a vessel 105 and a tube 111. The vessel 105 includes an edge 107, which seats against under the chin of the subject to define a chamber at an external location approximately at the internal soft tissue of the subject associated with the anterior triangle of the neck. The vessel 105 covers the soft tissue of the subject's anterior triangle of the neck in the range of about 32.9 cm$^2$ to about 210.58 cm$^2$. The range may cover the anatomical variations of the user population. The edge 107 helps to seal the vessel 105 on the surface of the skin of the subject and obviates the need for a strap. In this embodiment, the negative pressure exerted by a vacuum source holds the vessel 105 in place.

Figure 1C:
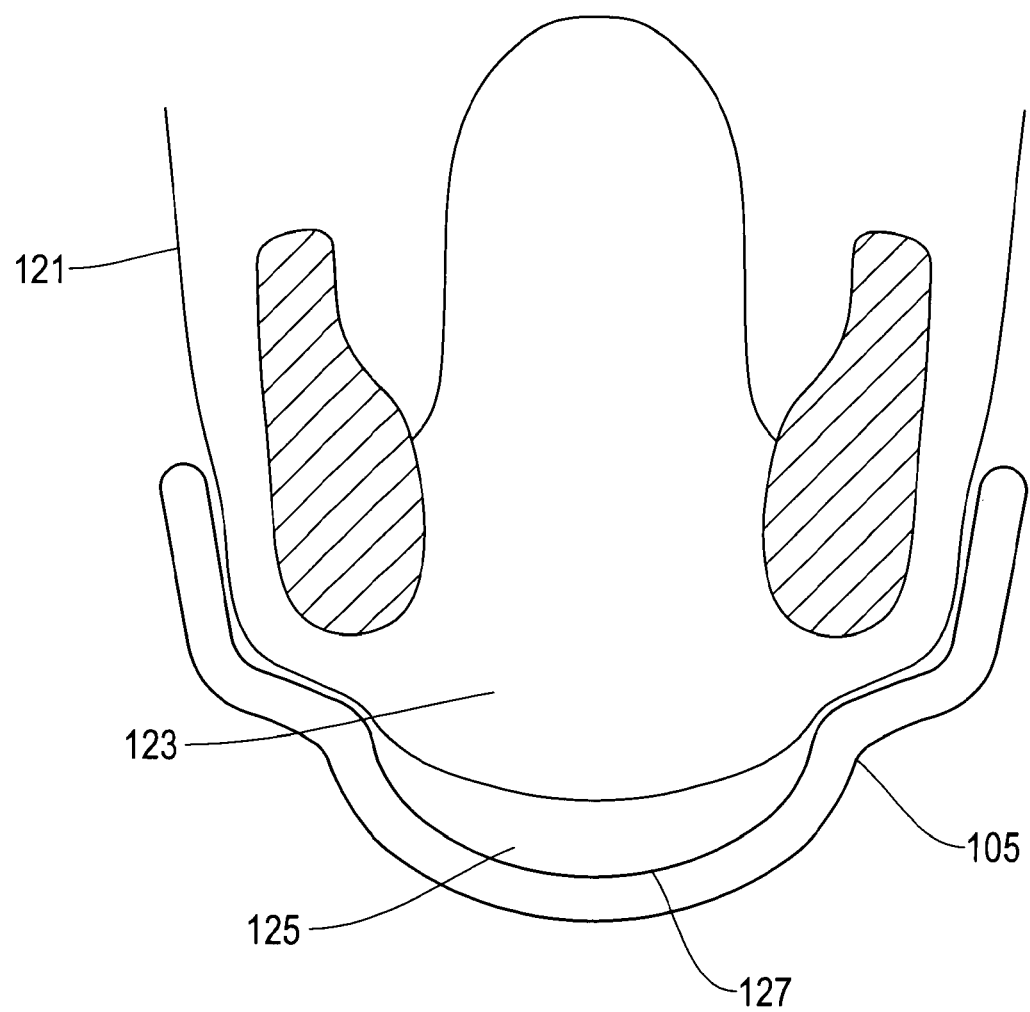
FIG. 1C is an axial view of the device of FIG. 1A on a subject.

Turning now to FIG. 1C, shown is an axial view of the device of FIG. 1A on a subject. In the shown embodiment, the vessel 105 is placed against the surface of the subject's skin 121 at the subject's mandible 123. A vacuum cavity 125 is created between the subject's skin 121 and the vessel's interior surface 127. The vacuum cavity 125 allows for the displacement of the soft tissue.

The vacuum source 109 creates negative pressure which is conveyed through the tube 111 to the vessel 105. Negative pressure means less than atmospheric pressure. This negative pressure, in conjunction with the area bounded by the seal, applies a force and consequently displaces the chin/neck soft tissues forward, thereby enlarging the airway passage in the back of the throat. According to the shown embodiment, the negative pressure created by the vacuum source 109 exerts negative pressure on a surface of the subject's skin.

Figure 1D:
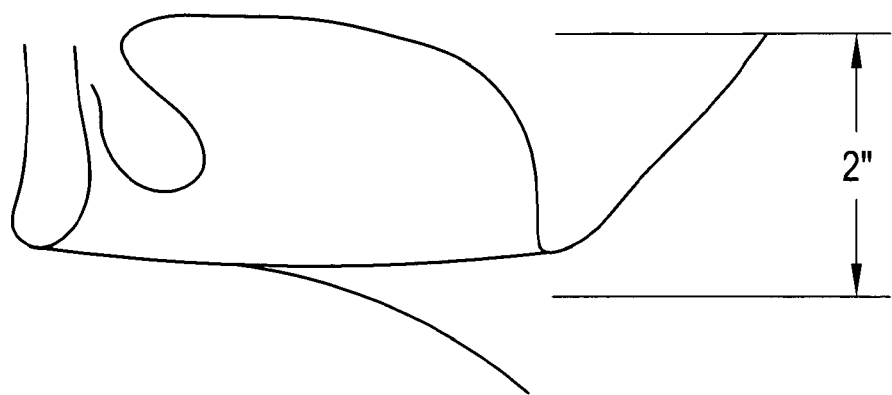
FIGS. 1D and 1E are a sagittal and a normal view of a subject's mandible, respectively.
Figure 1E:
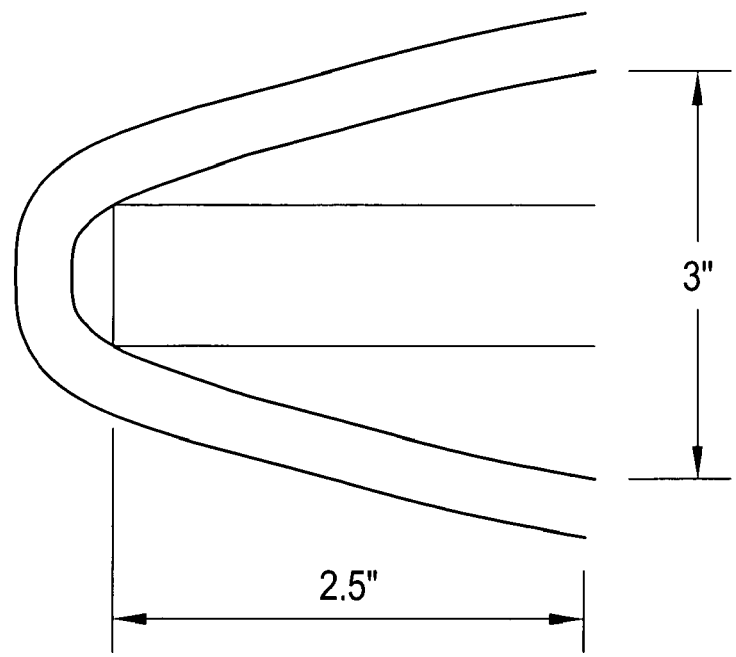

FIGS. 1D-1E show a few exemplary dimensions of a subject's mandible. Given the dimensions, the area and the volume of the soft tissue of the subject's mandible is about 32 cm$^2$ and about 163 cm$^3$, respectively. The weight of the mass of the subject's soft tissue is about 0.17 kg. The pressure to counter the weight of the subject's soft tissue is about 7.6 cm of water. The maximum effective pressure may depend on the subject's comfort threshold.

In one preferred embodiment, the aggregate force in the range of from about 0.5 kilogram to about 6.68 kilograms is applied to the interior of the vessel to pull the neck's anterior triangle toward the interior chamber. The aggregate force may preferably be in the range of about 0.61 kilograms to about 6.14 kilograms, and more preferably about 0.74 kilograms to 5.65 kilograms, and more preferably about 0.91 kilograms to about 5.2 kilograms, and more preferably from about 1.11 kilograms to about 4.78 kilograms.

Figure 1F:
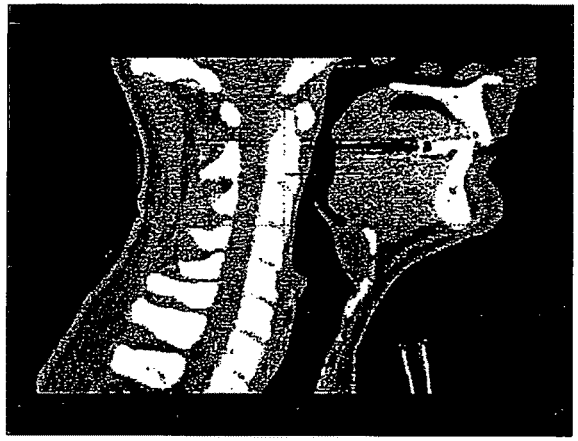
FIGS. 1F and 1G are CT scans of a sagittal and an axial view of a subject's upper airway, respectively, at an ambient pressure.
Figure 1G:
Figure 1H:
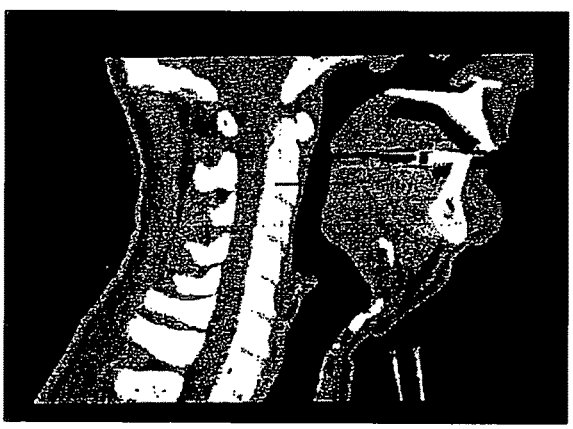
FIGS. 1H and 1I are CT scans of a sagittal and an axial view of a subject's upper airway, respectively, at 51 centimeters of water vacuum.
Figure 1I:
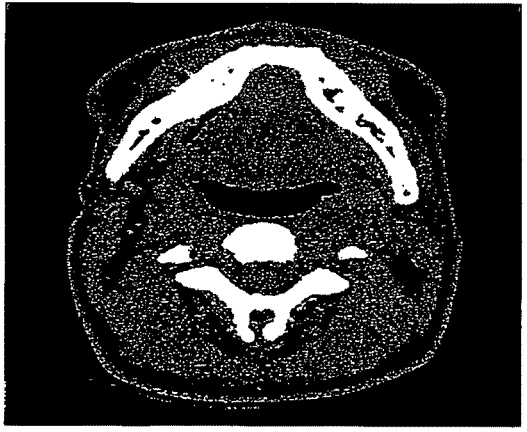

FIGS. 1F-1G show CT scans of the subject's upper airway at ambient pressure. FIGS. 1H-1I show the CT scans of the same subject with the negative pressure of 51 centimeters of water vacuum. As shown in the figures, there is an observable increase in the upper airway caliber. Pressures below about 7.62 centimeters of water vacuum may be ineffective since the pressure may be insufficient to maintain the vessel in the proper anatomic position. The pressures applied above about 60.96 centimeters of water vacuum may not be tolerable by a user since speaking and swallowing becomes difficult due to the high pressure.

The contact pressure applied to the subject's mandible varies depending on the contact area and the operating vacuum level of the vessel. At a given negative pressure value, for example 60 centimeters of water vacuum, by increasing the contact area between the vessel and the subject, the skin contact pressure is lowered and may enhance the comfort level for the subject.

The vacuum source 109 may be any type of pneumatic vacuum pump including a dynamic pump and a positive displacement pump. In one embodiment, the dynamic pump may be a regenerative pump or a centrifugal pump. The positive displacement pump may be a vane pump, a diaphragm pump, or a linear pump. In other embodiments, the pneumatic vacuum pump may be of any pump that creates a vacuum. In one embodiment, the pneumatic vacuum pump can provide up to 137 centimeters water vacuum. Additionally, in an embodiment, the pneumatic vacuum pump can operate at less than 25 dB sound pressure. In a further embodiment, the pneumatic vacuum pump creates no dynamic pressure ripple. In an additional embodiment, the pneumatic vacuum pump has a controller for regulating the vacuum level conveyed. Preferably the pneumatic vacuum pump contains all of these features.

The edge 107 of the vessel 105 may be coated or covered with a means for low pressure skin contact. In one embodiment, the low pressure skin contact means is an air-tube that traverses the periphery of the vessel. When negative pressure is applied by the vacuum source 109, the low pressure skin contact means will compress slightly. In one embodiment, the air-tube is inflated with a fixed amount of air. In an alternate embodiment, the air-tube is inflated with the exhaust emitted by the pneumatic vacuum pump. Additionally, the low pressure skin contact means could include without limitation a soft material such foam, rubber, fabric, adhesive, and the like. Additionally, the edge 107 can extend around the full periphery of the vessel 105 including around bellows 119. In alternative embodiments, the edge 107 may not include a means for low pressure contact. The edge 107 may simply be the periphery of the material that comprises the vessel 105 or the vessel 105 and the bellows 119.

In an alternative embodiment, the device 101 may have an auto adjust feature or a controller which would maintain the vacuum level just low enough to eliminate snoring and/or an apnea event. The pneumatic vacuum pump would have at least one acoustic sensor that would listen to the acoustic signature emitted of the user coming back up the tube 111. The acoustic sensor according to any of the embodiments of the present invention may be any acoustic sensor such as a microphone, or the like. In one embodiment, the acoustic sensor is in the vessel 105 itself. In alternative embodiments, the acoustic sensor could located anywhere on the device 101. Signal processing would cue a microprocessor to adjust the pressure from the pneumatic vacuum pump to a desired level. The objective is to enhance patient comfort by optimizing the level of negative pressure.

Figure 2:
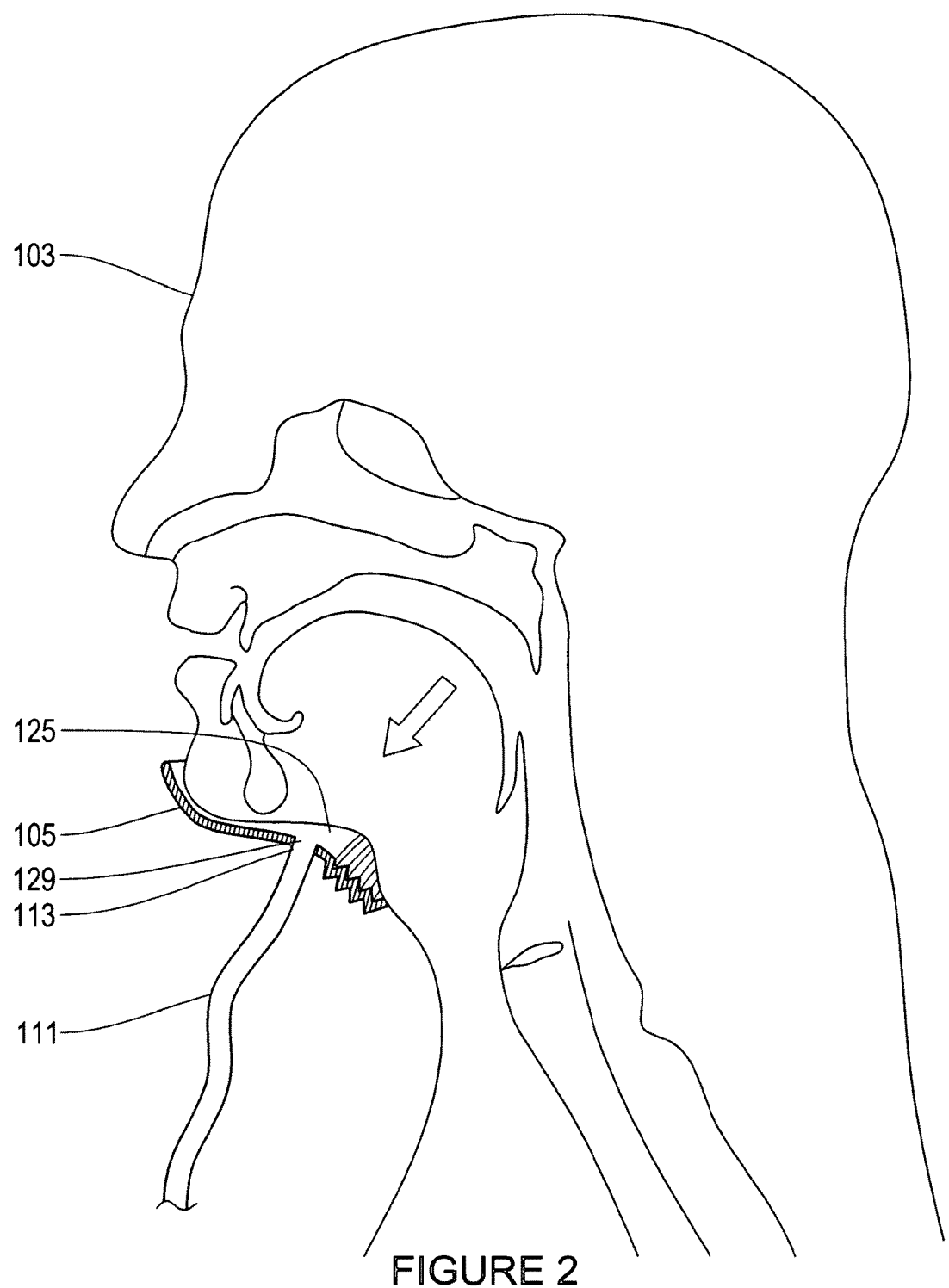
FIG. 2 is a sagittal view of a subject using the device of FIG. 1A.

Turning to FIG. 2, shown is a sagittal view of a subject using the device of FIG. 1A. In the embodiment shown, the natural anatomical contours of the subject form a seal with the vessel 105.

As shown in FIG. 2, the vessel 105 has an opening 129. The tube's first end 113 is attached to the vessel 105 at the opening 129. Accordingly, as shown, negative pressure may be generated at the vacuum source (not shown) and conveyed through the tube 111. The negative pressure in the vacuum cavity causes negative pressure to be exerted on the area of skin exposed therein. The negative pressure displaces the subject's soft tissue, resulting in an opened stricture or airway. Accordingly, the subject 103 has an airway that is open and free of obstruction.

Figure 3:
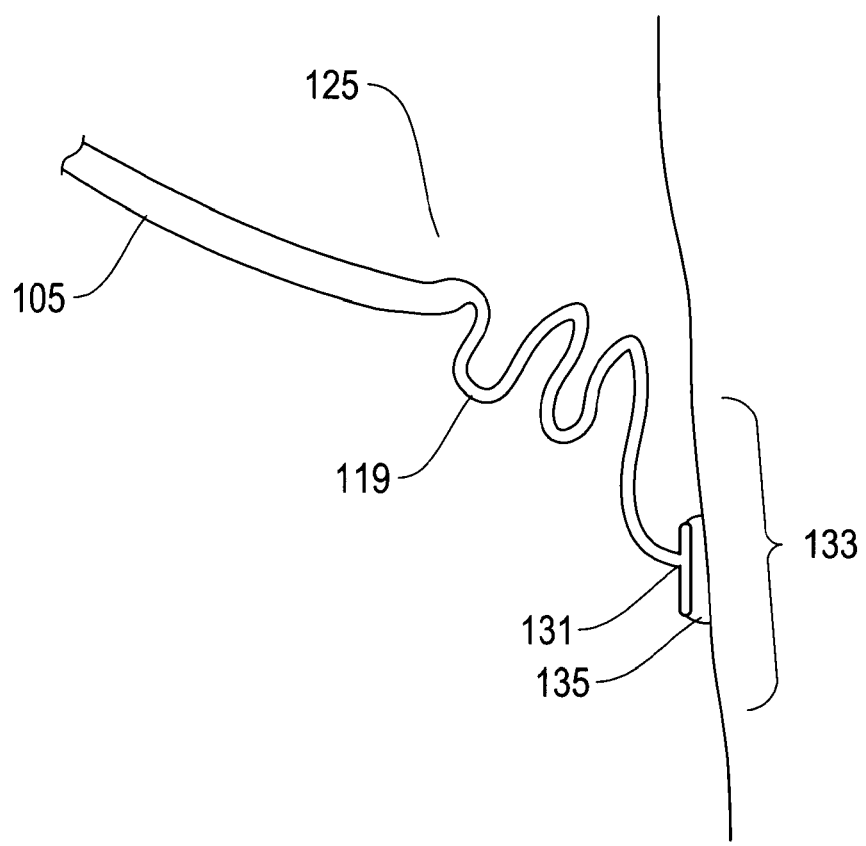
FIG. 3 is an exploded partial cross-sectional view the vessel according to an embodiment of the present invention.

Referring now to FIG. 3, shown is an exploded partial cross-sectional view the device of FIG. 2. In the embodiment shown, a differential clamp 131 is attached to the bellows 119. The vessel 105 forms a seal with the subject's neck at a differential clamp-on area 133. The differential clamp 131 has a low friction surface 135 that helps form the seal at a differential clamp-on area 135. The differential clamp 131 is just one means for low pressure skin contact. In alternative embodiments, it is possible to utilize other clamps similar to differential clamps. Additionally, in alternative embodiments, adhesive may cover the surface of the clamp. As a seal is formed, a low pressure environment is created in the vacuum cavity 125.

The differential clamp-on area 133 includes both the point at which the differential clamp 131 makes contact with a subject's skin, as well as the area surrounding the point of contact. In the differential clamp-on area 133 area, the contact pattern along a subject's neckline becomes shifted downwards rather than being in line with the convolutions of the bellows 119. As a negative or low pressure exists between the neck and the differential clamp 131 in the vacuum cavity 125, a natural force is carried into the low friction surface 135 against the neck. Accordingly, an additional force is created on the neck that maintains a seal. Therefore, in the differential clamp-on area 133, the contact pattern along a subject's neckline is moved such that the natural hydraulic forces, or the difference of the pressures existing in normal atmospheric pressure and the negative or low pressure existing in the vacuum cavity 125 will create an additional load onto the actual seal itself point where the low friction surface 135 makes contact with a subject's neck.

Figure 4A:
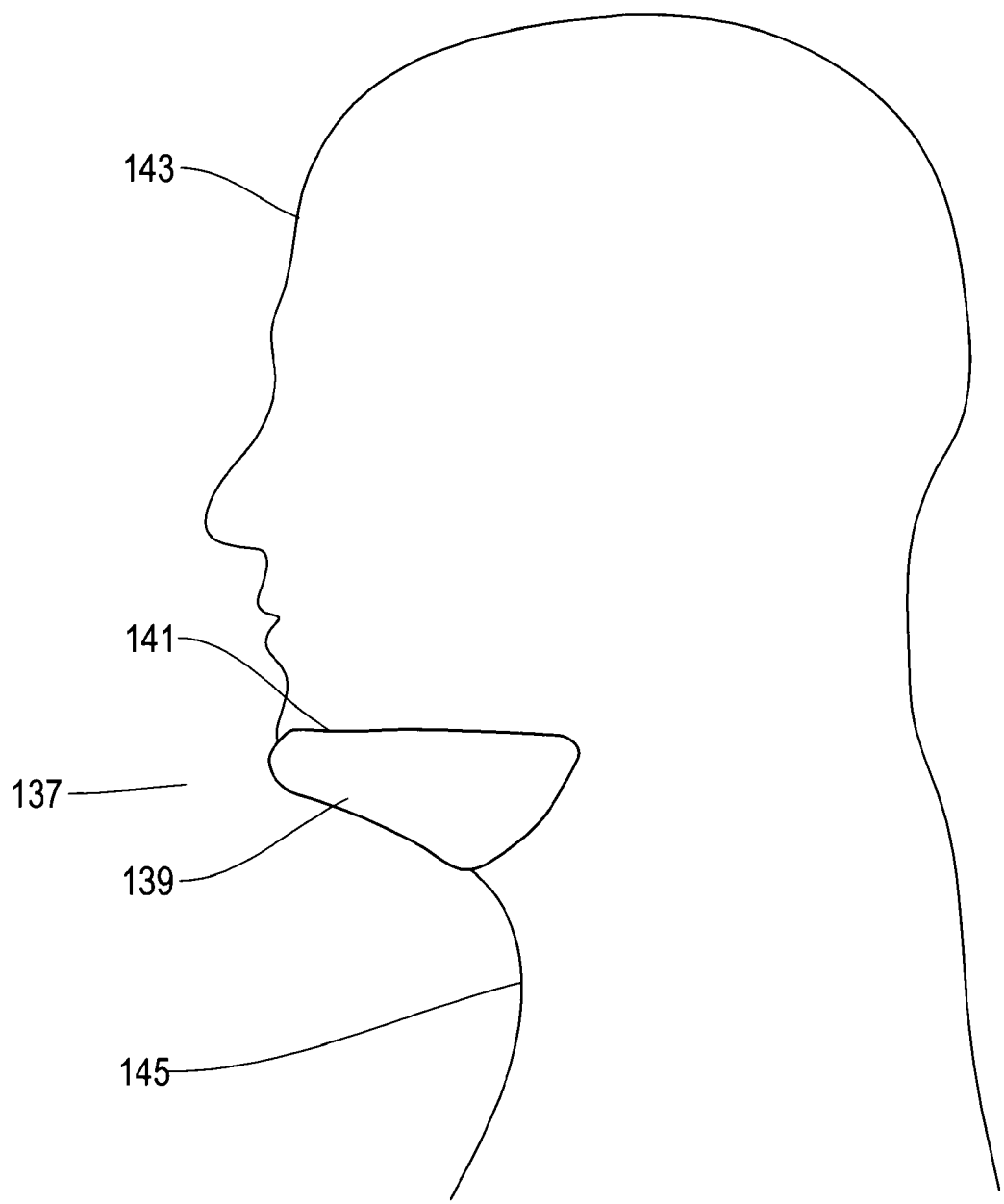
FIG. 4A is a view of the device according to an embodiment of the present invention on a subject.

Turning now to FIG. 4A, shown is a view of a device 137 according to an embodiment of the present invention on a subject. The device 137 has a vessel 139. The vessel 139 has an edge 141, and an internal surface (not shown). The vessel 139 is configured to fit under the chin of a subject 143 adjacent to the subject's neck at an external location corresponding approximately with the subject's internal soft tissue associated with the neck's anterior triangle.

The vessel 139 is fabricated or formed from a material having a resilient memory. Accordingly, the vessel returns to its original form or position after being bent, compressed, or stretched. The vessel 139 can be made of any material having a resilient memory including, but not limited to, plastics, metals, fabrics, polymers, rubbers, and the like.

An adhesive (not shown) coats at least a portion of the internal surface 147 of the vessel 139 to form a seal against the skin 145 of a subject 143.

Figure 4B:
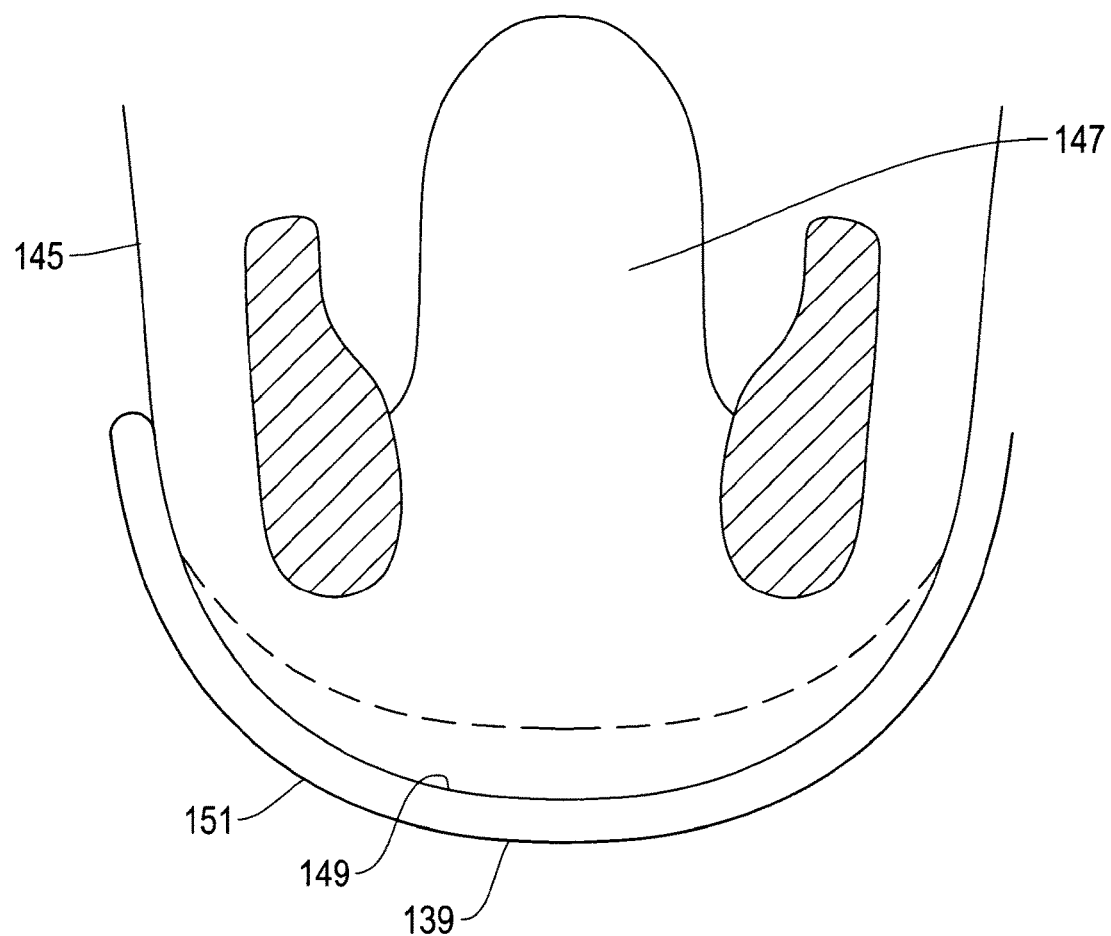
FIG. 4B is an axial view of the device of FIG. 4A on a subject.

Referring next to FIG. 4B, shown is an axial view of the device of FIG. 4A on a subject. In the shown embodiment, the vessel 139 is placed against the surface of the subject's skin 145 at the subject's mandible 147. An adhesive coats at least a portion of the internal surface 149 of the vessel 139.

In the embodiment shown in FIG. 4B, one process for applying the vessel 139 comprises applying pressure on the exterior surface 151 of the vessel 139 at a point approximately central to vessel 139 causing it to invert. The inverted vessel 139 is placed under the chin of the subject 143 adjacent to the subject's neck at an external location corresponding approximately with the subject's internal soft tissue associated with the neck's anterior triangle. After placement on the subject, the pressure applied to the central point of the vessel 139 is removed such that the flexible vessel returns to its original shape thereby taking hold of the skin 145 in contact with the adhesive. As a result, the skin 145 in contact with the adhesive will be displaced. Accordingly, the subject's internal soft tissue is displaced in a forward and downward fashion, thereby enhancing the airway.

According to another embodiment of the present invention, the vessel 139 may be provided without any adhesive on it at all. Accordingly, adhesive could be independently applied to the skin 145 of the subject 143 in a desired area and the vessel 139 could be applied to the coated skin in the manner provided above. In one embodiment, the adhesive could be double sided tape.

Figure 5:
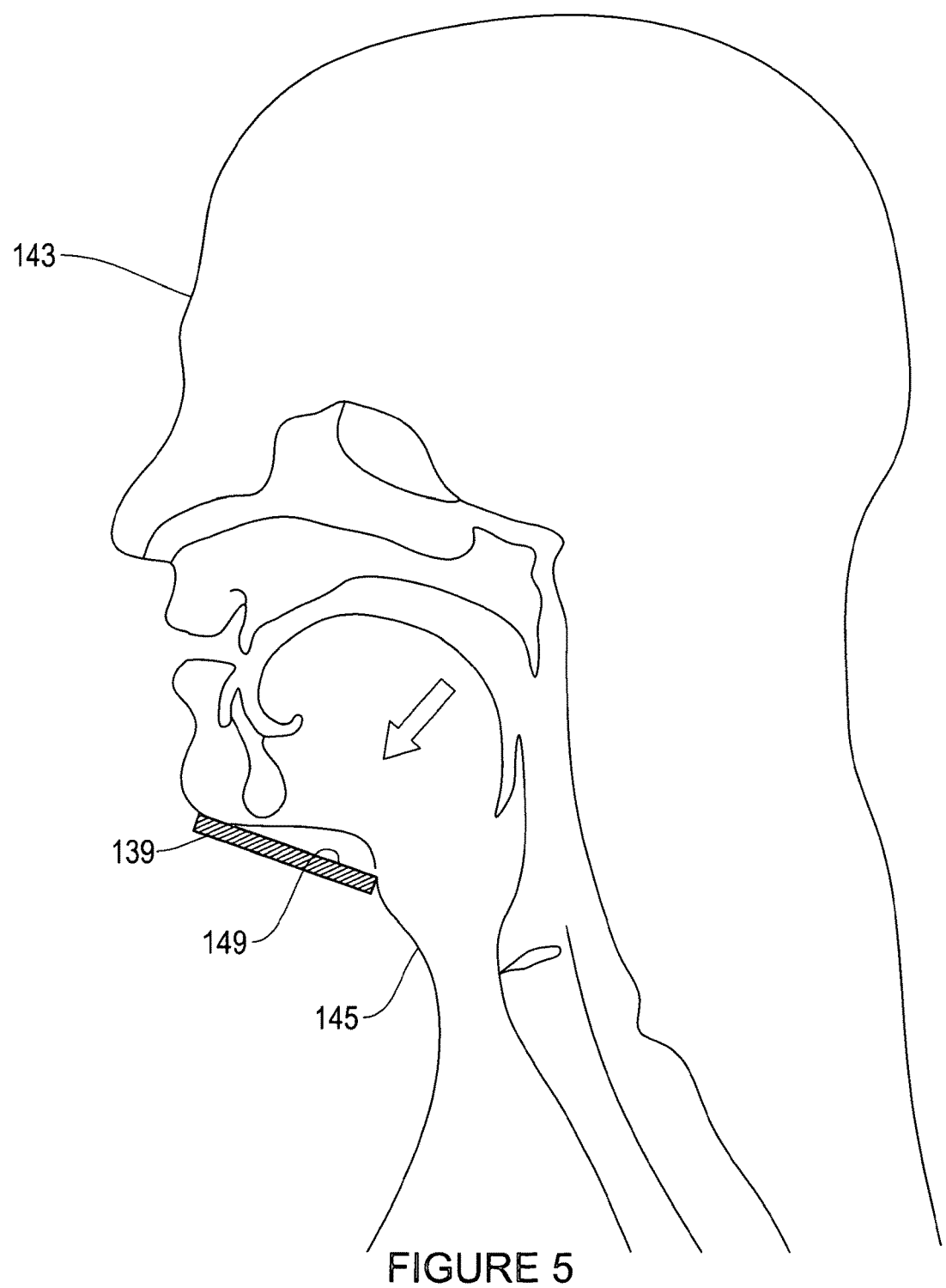
FIG. 5 is a sagittal view of a subject using the device of FIG. 4A.

Turning now to FIG. 5, shown is a sagittal view of a subject using the device of FIG. 4A. The vessel 139 has an adhesive on at least a portion of its internal surface 149. In contact with the skin, the vessel 139 pulls the subject's skin. The pulling displaces the subject's soft tissue, resulting in an opened stricture. Accordingly, the subject 143 has an airway that is open and free of obstruction.

Figure 6:
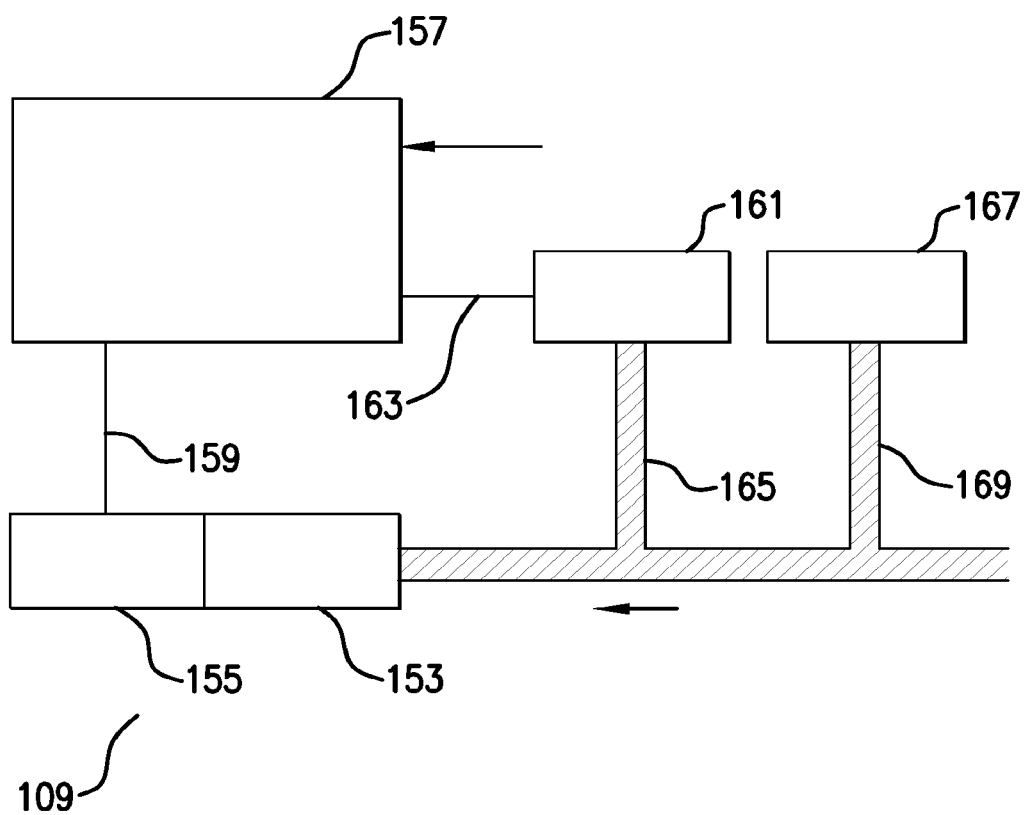
FIG. 6 is a schematic representation of an embodiment of the vacuum source according to the device of FIG. 1A.

Referring now to FIG. 6, shown is a schematic representation of an embodiment of the vacuum source according to the device of FIG. 1A. In the embodiment shown, the vacuum source 109 has a vacuum pump 153 attached to a motor 155. A microcontroller 157, such as a microprocessor, is attached to the motor 155 by a first electrical connection 159. A pressure sensor 161 is attached to the microcontroller 157 by a second electrical connection 163. Additionally, a tube 111 connects the vessel (not shown) to the vacuum pump at opposite ends of the tube 111. A first pneumatic connection 165 attaches the tube 111 to the pressure sensor 161. A relief valve 167 is attached to the tube 111 by a second pneumatic connection 169.

According to an embodiment of the present invention, the vacuum pump 153 may be any type of pneumatic vacuum pump including, but not limited to, a regenerative pump, a vane pump, a diaphragm pump, a centrifugal pump, a positive displacement pump or a dynamic pump. In one embodiment, the pneumatic vacuum pump can provide up to 137 centimeters water vacuum. The microcontroller 157 may be any controller capable of identifying and processing data and/or signals received from the motor 155 and vacuum pump 153 and/or the pressure sensor 161 to regulate the vacuum pressure or negative pressure generated. The relief valve 167 may be mechanically or manually operated. The relief valve used to control or limit the negative pressure being exerted by the motor 155 and vacuum pump 153 which can build up by allowing the pressure to flow therefrom.

According to one embodiment of the present invention, a user sets an initial vacuum level of the device. Until the vessel 109 is in place and engaged in a desired position the pressure sensor 163 will recognize low vacuum levels. The microcontroller 157 will speed up the motor 155 and vacuum pump 153 until a set vacuum value or desired level of negative pressure is achieved in the vacuum cavity (not shown) of the vessel (not shown). If a vacuum value or desired level of negative pressure is surpassed, the microcontroller 157 will electrically slow the motor 155 and vacuum pump 153 down. The set vacuum level or desired level of negative pressure is automatically maintained by the microcontroller. To make up for system leakage, the motor 155 and vacuum pump 153 will rotate slowly thereby making up for system leakage. Accordingly, the device will operate quietly.

The present invention is also drawn to various methods for using the devices for opening an airway.

In accordance with a further embodiment of the present invention, a method of opening an airway is provided. According to the method, a device is placed against a surface of a subject's neck. The device has a vessel having an edge and an internal surface. The device is configured to fit under the chin of a subject adjacent to the subject's neck at an external location corresponding approximately with the subject's internal soft tissue associated with the neck's anterior triangle. The device applies negative pressure on the surface of the subject's neck, thereby opening the airway. The device is preferably a device as described herein with respect to other embodiments of the present invention.

In accordance with yet still another embodiment of the present invention, a method of opening an airway is provided. According to the method, a vessel is placed on the surface of a subject's neck. The vessel has an edge and an internal surface. The vessel is configured to fit under the chin of the subject adjacent to the subject's neck at an external location corresponding approximately with the subject's internal soft tissue associated with the neck's anterior triangle. The vessel is connected to a source of negative pressure. A force is applied in the range of from about 0.5 kilogram to 6.68 kilograms to the anterior triangle of the subject's neck to pull the soft tissue toward the interior chamber. The device is preferably a device as described herein with respect to other embodiments of the present invention.

An alternative embodiment of the present invention provides a method of opening an airway. A flexible vessel with a resilient memory having an edge, an internal surface, an external surface, and a central point is provided. The internal surface is at least partially coated with adhesive. Applying pressure on the exterior surface at the central point of the flexible vessel causes it to invert. The inverted flexible vessel is placed under the chin of a subject adjacent to the subject's neck at an external location corresponding approximately with the subject's internal soft tissue associated with the neck's anterior triangle. The pressure applied to the central point of the flexible vessel is removed such that the flexible vessel returns to its original shape. The device is preferably a device as described herein with respect to other embodiments of the present invention.

In accordance with yet another embodiment of the present invention, a method of reducing snoring is provided. According to the method, a vessel having an opening is placed on the surface of a subject's neck. The vessel is configured to fit under the chin of a subject adjacent to the subject's neck at an external location corresponding approximately with the subject's internal soft tissue associated with the neck's anterior triangle. The vessel is attached at the opening to a tube having a first end and a second end. The first end of the tube is attached at the opening. Additionally, a vacuum source is attached to the second end of the tube. The vacuum source has a microprocessor and at least one acoustic sensor connected thereto. Negative pressure is created at the vacuum source. A signal corresponding with an acoustic signature of the subject is identified by the acoustic sensor. The signal is registered and processed with a microprocessor attached to the vacuum source. The level of pressure created at the vacuum source is automatically maintained to reduce and/or eliminate snoring. The device is preferably a device as described herein with respect to other embodiments of the present invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed:

1. A therapeutic apparatus for relieving obstruction to the upper airway of a patient, comprising:
    a vessel having a vessel edge and a vessel internal surface, the vessel edge configured to seat against the chin and neck of the patient, thereby defining a chamber at an external location of the patient associated with the anterior triangle of the neck;
    a means for reducing contact pressure of the vessel and the neck of the patient, wherein the means for reducing contact pressure is unitary with and extends away from the vessel edge, the vessel edge and means for reducing contact pressure being configured to seat against the chin and neck of the patient to define the chamber at an external location approximately at the internal soft tissue of the patient associated with the anterior triangle of the neck and to create a seal with the skin of the patient upon application of a negative pressure within the chamber; and
    a means for producing a negative pressure within the chamber to apply a force of 0.5 kg to 6.68 kg to a surface of the neck of the patient.

2. A therapeutic apparatus according to claim 1, wherein the means for reducing contact pressure comprises an elastomeric external flap extending from said vessel edge, wherein said elastomeric external flap forms a sealing surface, and wherein said elastomeric external flap is configured such that, in use, the sealing surface contacts the neck of the patient.

3. A therapeutic apparatus according to claim 2, wherein the means for producing a negative pressure is a positive displacement pump.

4. A therapeutic apparatus according to claim 3, wherein the means for producing a negative pressure is a diaphragm pump, a vane pump, or a linear pump.

5. A therapeutic apparatus according to claim 2, wherein said sealing surface comprises an adhesive on at least a portion of the sealing surface.

6. A therapeutic apparatus according to claim 2, wherein the sealing surface comprises a foam material on at least a portion of the sealing surface.

7. A therapeutic apparatus according to claim 2, wherein the sealing surface comprises a fabric material on at least a portion of the sealing surface.

8. A therapeutic apparatus according to claim 2, wherein the elastomeric external flap extends around the full periphery of the vessel.

9. A therapeutic apparatus according to claim 2, wherein the means for producing a negative pressure is a dynamic pump.

10. A therapeutic apparatus according to claim 2, wherein the means for producing a negative pressure comprises a vacuum pump and a controller for regulating a vacuum level to maintain the force within the 0.5 kg to 6.68 kg range.

11. A therapeutic apparatus according to claim 1, wherein the means for producing a negative pressure is a positive displacement pump.

12. A therapeutic apparatus according to claim 11, wherein the means for producing a negative pressure is a diaphragm pump, a vane pump, or a linear pump.

13. A therapeutic apparatus according to claim 1, wherein the means for producing a negative pressure is a dynamic pump.

14. A therapeutic apparatus according to claim 1, wherein the means for producing a negative pressure comprises a vacuum pump and a controller for regulating a vacuum level to maintain the force within the 0.5 kg to 6.68 kg range.

15. A therapeutic apparatus according to claim 1, wherein the means for producing a negative pressure is connected to the vessel by a tube which operably connects an opening within the vessel internal surface to the means for producing a negative pressure.

16. A therapeutic apparatus according to claim 1, wherein the vessel comprises a surface made from silicone, urethane or rubber.

17. A method for maintaining airway patency in a patient, comprising:
    providing a therapeutic apparatus for relieving obstruction to the upper airway of a patient, comprising:
        a vessel having a vessel edge and a vessel internal surface, the vessel edge configured to seat against the chin and neck of the patient, thereby defining a chamber at an external location of the patient associated with the anterior triangle of the neck,
        a means for reducing contact pressure of the vessel and the neck of the patient, wherein the means for reducing contact pressure is unitary with and extends away from the vessel edge, the vessel edge and means for reducing contact pressure being configured to seat against the chin and neck of the patient to define the chamber at an external location approximately at the internal soft tissue of the patient associated with the anterior triangle of the neck and to create a seal with the skin of the patient upon application of a negative pressure within the chamber, and
        a means for producing a negative pressure within the chamber to apply a force of 0.5 kg to 6.68 kg to a surface of the neck of the patient;
    mating the vessel to the neck of the patient; and
    causing the means for producing a negative pressure within the chamber to apply the force of 0.5 kg to 6.68 kg to the surface of the neck of the patient.

18. A method for maintaining airway patency in a patient, comprising:
    providing a therapeutic apparatus for relieving obstruction to the upper airway of a patient, comprising:
        a vessel having a vessel edge and a vessel internal surface, the vessel edge configured to seat against the chin and neck of the patient, thereby defining a chamber at an external location of the patient associated with the anterior triangle of the neck,
        a means for reducing contact pressure of the vessel and the neck of the patient, wherein the means for reducing contact pressure is unitary with and extends away from the vessel edge, wherein the means for reducing contact pressure comprises an elastomeric external flap extending from said vessel edge, wherein said elastomeric external flap forms a sealing surface, and wherein said elastomeric external flap is configured such that, in use, the sealing surface contacts the neck of the patient, and a means for producing a negative pressure within the chamber to apply a force of 0.5 kg to 6.68 kg to a surface of the neck of the patient;

mating the vessel to the neck of the patient; and causing the means for producing a negative pressure within the chamber to apply the force of 0.5 kg to 6.68 kg to the surface of the neck of the patient.

\* \* \* \* \*